United States Patent
Zerfas et al.

(10) Patent No.: US 8,358,890 B2
(45) Date of Patent: Jan. 22, 2013

(54) METHOD AND APPARATUS RELATED TO A SIDE-FIRE MEMBER HAVING A DOPED SILICA COMPONENT

(75) Inventors: Jeffrey W. Zerfas, Bloomington, IN (US); Richard P. Tumminelli, Ashland, MA (US)

(73) Assignees: Boston Scientific Scimed, Inc., Maple Grove, IN (US); Coherent, Inc., Santa Clara, CA (US)

(*) Notice: Subject to any disclaimer, the term of this patent is extended or adjusted under 35 U.S.C. 154(b) by 63 days.

(21) Appl. No.: 12/948,138

(22) Filed: Nov. 17, 2010

(65) Prior Publication Data

US 2011/0176770 A1 Jul. 21, 2011

Related U.S. Application Data

(60) Provisional application No. 61/262,397, filed on Nov. 18, 2009.

(51) Int. Cl.
- G02B 6/26 (2006.01)
- A61B 18/18 (2006.01)
- A61B 1/00 (2006.01)

(52) U.S. Cl. .............. 385/39; 385/95; 385/96; 385/115; 385/116; 385/117; 385/119; 385/15; 385/31; 385/33; 385/38; 385/34; 385/35; 606/2; 606/4; 606/15; 606/16; 606/17; 606/18; 600/101

(58) Field of Classification Search .............. 385/95–96, 385/115–117, 119, 15, 31, 33–35, 38–39; 606/2, 4, 15–18; 600/101
See application file for complete search history.

(56) References Cited

U.S. PATENT DOCUMENTS

| | | | |
|---|---|---|---|
| 4,737,011 A | 4/1988 | Iri et al. | |
| 5,428,699 A | 6/1995 | Pon | |
| 5,437,660 A | 8/1995 | Johnson et al. | |
| 5,509,917 A | 4/1996 | Cecchetti et al. | |
| 5,537,499 A | 7/1996 | Brekke | |
| 5,562,657 A * | 10/1996 | Griffin | 606/17 |
| 5,649,924 A | 7/1997 | Everett et al. | |

(Continued)

FOREIGN PATENT DOCUMENTS

WO  WO 2006/138128 A2  12/2006

(Continued)

OTHER PUBLICATIONS

International Search Report and Written Opinion issued in corresponding application PCT/US2010/056947, mailed on Mar. 16, 2011, 11 pages.

Primary Examiner — Brian M. Healy
Assistant Examiner — Guy Anderson
(74) Attorney, Agent, or Firm — Bookoff McAndrews, PLLC (57) ABSTRACT

In one embodiment, an apparatus may include an optical fiber that may have a surface non-normal to a longitudinal axis of a distal end portion of the optical fiber. The surface may define a portion of an interface configured to redirect electromagnetic radiation propagated from within the optical fiber and incident on the interface to a direction offset from the longitudinal axis. The apparatus may also include a doped silica cap that may be fused to the optical fiber such that the surface of the optical fiber may be disposed within a cavity defined by the doped silica cap.

20 Claims, 5 Drawing Sheets

U.S. PATENT DOCUMENTS

| | | | |
|---|---|---|---|
| 5,833,683 | A | 11/1998 | Fuller et al. |
| 6,282,349 | B1 | 8/2001 | Griffin |
| 6,296,608 | B1 | 10/2001 | Daniels et al. |
| 6,347,178 | B1 | 2/2002 | Edwards et al. |
| 6,554,824 | B2 | 4/2003 | Davenport et al. |
| 6,565,555 | B1 | 5/2003 | Ryan et al. |
| 6,606,431 | B2 | 8/2003 | Unsworth |
| 6,986,764 | B2 | 1/2006 | Davenport et al. |
| 7,169,140 | B1 | 1/2007 | Kume |
| 7,228,033 | B2 * | 6/2007 | Bhagavatula et al. .......... 385/35 |
| 7,238,182 | B2 | 7/2007 | Swoyer et al. |
| 7,447,409 | B2 | 11/2008 | Griffin |
| 2006/0078265 | A1 | 4/2006 | Loeb |
| 2007/0106286 | A1 | 5/2007 | Harschack et al. |
| 2007/0179485 | A1 | 8/2007 | Yeik et al. |
| 2007/0189683 | A1 | 8/2007 | Griffin |
| 2008/0247714 | A1 * | 10/2008 | Nakamura et al. .............. 385/96 |
| 2009/0175576 | A1 * | 7/2009 | Tang ................ 385/31 |
| 2009/0210242 | A1 * | 8/2009 | Black et al. ....................... 705/1 |
| 2009/0299352 | A1 * | 12/2009 | Zerfas et al. .................... 606/15 |
| 2010/0198009 | A1 | 8/2010 | Farr et al. |

FOREIGN PATENT DOCUMENTS

| WO | WO 2007/089722 A2 | 8/2007 |
|---|---|---|

\* cited by examiner

METHOD AND APPARATUS RELATED TO A SIDE-FIRE MEMBER HAVING A DOPED SILICA COMPONENT

CROSS REFERENCE TO RELATED APPLICATION

This Nonprovisional Patent Application claims the benefit of priority under 35 U.S.C. §119 to U.S. Provisional Patent Application No. 61/262,397, filed Nov. 18, 2009, and titled "METHODS AND APPARATUS RELATED TO A SIDE-FIRE MEMBER HAVING A DOPED SILICA COMPONENT," which is incorporated herein by reference.

FIELD

Embodiments relate generally to optical medical devices, and, in particular, to side-firing optical fibers and methods for using such devices.

BACKGROUND

During some laser-based surgical procedures, a side-firing optical fiber can provide a medical practitioner with more control when applying laser energy to a treatment area than a straight-firing optical fiber. Passing the distal end portion of the side-firing optical fiber through an endoscope during surgery, however, may damage, scratch, degrade, and/or deform the distal end portion. A capillary and/or a metal cap or cannula, usually made of surgical (e.g., medical) grade stainless steel and having a transmissive window, made of an optically transmissive material, can be placed over the distal end portion of the side-firing optical fiber to protect the distal end portion. Once the distal end portion is properly positioned for treatment, laser energy can be applied via the side-firing optical fiber to the target area.

During use of the device, a portion of the laser energy can leak into the capillary and/or the metal cap at the distal end portion of the side-firing optical fiber. This leakage of laser energy can reduce the efficiency with which laser energy is delivered to the treatment area and/or increase overheating of the metal cap that is typically used to protect the distal end portion. In some instances, overheating that can result from laser energy leakage can affect the mechanical and/or optical properties of the side-firing optical fiber. In other instances, the overheating that can occur from the laser energy leakage can be sufficiently severe to damage the capillary and/or the metal cap at the distal end portion of the side-firing optical fiber.

Thus, a need exists for a side-firing optical fiber distal end portion that can increase device longevity, increase laser energy transmission efficiency, reduce overheating, and/or increase patient safety.

SUMMARY

In one embodiment, an apparatus may include an optical fiber that may have a surface non-normal to a longitudinal axis of a distal end portion of the optical fiber. The surface may define a portion of an interface which may be configured to redirect electromagnetic radiation propagated from within the optical fiber and incident on the interface to a direction offset from the longitudinal axis. The apparatus may also include a doped silica cap that may be fused to the optical fiber such that the surface of the optical fiber may be disposed within a cavity defined by the doped silica cap.

In some embodiments, the surface and the doped silica cap may define an enclosure. In some embodiments, the doped silica cap may have an index of refraction less than an index of refraction associated with a cladding layer of the optical fiber. In some embodiments, the doped silica cap may be fused to a cladding layer of the optical fiber.

In some embodiments, the doped silica cap may be adhesively coupled to a cladding layer of the optical fiber. In some embodiments, the doped silica cap may be fused to an outer-layer portion of the optical fiber. The doped silica cap may be a fluorine-doped silica cap which may have a concentration of fluorine greater than a concentration of fluorine of the outer-layer portion of the optical fiber.

In some embodiments, the interface may be a first interface and the doped silica cap may be fused to a cladding layer of the optical fiber. The doped silica cap and the cladding layer may define a second interface such that electromagnetic radiation propagated within the cladding layer and incident on the second interface may be substantially internally reflected within the cladding layer.

In some embodiments, the surface may be disposed within a distal end portion of the doped silica cap and a proximal end portion of the doped silica cap may be fused to the optical fiber. In some embodiments, the surface may be included in the distal end portion of the optical fiber. In addition, the doped silica cap may be fused to a portion of the optical fiber proximal to the distal end portion of the optical fiber without being fused to the distal end portion of the optical fiber.

In some embodiments, the apparatus may include a metallic cap coupled to the doped silica cap. The metallic cap may have an inner surface configured to redirect electromagnetic radiation incident on the inner surface of the metallic cap into the cavity defined by the doped silica cap.

In some embodiments, the apparatus may include a metallic cap coupled to the doped silica cap. The metallic cap may have an opening aligned with the direction such that the electromagnetic radiation may be transmitted through the opening.

In another embodiment, a method includes receiving an optical fiber that may have a surface non-normal to a longitudinal axis of a distal end portion of the optical fiber. A doped silica component may be moved over the surface of the optical fiber such that the surface of the optical fiber may be disposed within a bore. The method may also include heating the doped silica component and the optical fiber such that at least a portion of an inner surface of the doped silica component defined by the bore may be fused to at least a portion of an outer surface of the optical fiber.

In some embodiments, the moving may include moving until the surface of the optical fiber may be disposed within the bore of the doped silica component. In some embodiments, the portion of the inner surface of the doped silica component defined by the bore may be included in a proximal end of the doped silica component. In addition, the bore of the doped silica component may be a bore therethrough. The method may also include defining an enclosure at a distal end of the doped silica component.

In some embodiments, the portion of the inner surface of the doped silica component defined by the bore may be included in a proximal end of the doped silica component. The bore of the doped silica component may be a bore therethrough. The method may also include heating a distal end of the doped silica component such that an enclosure may be defined by the distal end of the doped silica component and the optical fiber.

In some embodiments, the doped silica component may be cut from a fluorine-doped preform. In addition, the outer surface of the optical fiber may be associated with a fluorine-doped cladding layer. In some embodiments, the heating may define an interface and the doped silica component may have a doping concentration such that electromagnetic radiation from the optical fiber and incident on the interface may be substantially internally reflected.

In some embodiments, the method may include moving an outer cap over the doped silica component. The outer cap may be substantially opaque to laser energy transmitted from the optical fiber.

In some embodiments, the surface may define a portion of an interface configured to redirect electromagnetic radiation propagated from within the silica-based optical fiber and incident on the interface to a lateral direction offset from the longitudinal axis. The method may also include moving an outer cap over the doped silica component such that an opening defined by the outer cap may be aligned with the lateral direction. In some embodiments, the doped silica component may be a doped silica cap.

In another embodiment, an apparatus includes a doped silica cap and a distal end portion of an optical fiber that may have a surface disposed within the doped silica cap. The surface may define at least a portion of an interface configured to redirect laser energy from a first portion of an optical path to a second portion of the optical path non-parallel to the first portion of the optical path. In addition, the second portion of the optical path may intersect an outer surface of the doped silica cap.

In some embodiments, at least a portion of an inner surface of the doped silica cap may be heat-fused to at least a portion of an outer surface of the distal end portion of the optical fiber. In some embodiments, at least a portion of an inner surface of the doped silica cap and at least a portion of an outer surface of the distal end portion of the optical fiber may define an interface. The doped silica cap may have a doping concentration such that electromagnetic radiation from the optical fiber and incident on the interface may be substantially internally reflected.

In some embodiments, at least a portion of the doped silica cap may be adhesively coupled to at least a portion of the distal end portion of the optical fiber. In some embodiments, the doped silica cap may be a fluorine-doped silica cap.

In some embodiments, the apparatus may also include an outer cap disposed over at least a portion of the doped silica cap. In addition, the outer cap may be substantially opaque to laser energy. In some embodiments, the apparatus may also include a metallic cap disposed over at least a portion of the doped silica cap. The second portion of the optical path may intersect an opening of the metallic cap.

In yet another embodiment, a method may include inserting a distal end portion of an optical fiber into a patient's body. The optical fiber may have a surface disposed within a doped silica cap. The surface may define at least a portion of an interface configured to redirect laser energy from a first portion of an optical path to a second portion of the optical path non-parallel to the first portion of the optical path. The method may also include, after the inserting, activating a laser source such that laser energy may be transmitted along the optical path into the patient's body. In some embodiments, the doped silica cap may be a fluorine-doped silica cap.

While various embodiments have been described above, it should be understood that they have been presented by way of example only, and not limitation. For example, the side-firing system described herein may include various combinations and/or sub-combinations of the components and/or features of the different embodiments described. Although described with reference to use for treatment of symptoms related to BPH, it should be understood that the side-firing system and the side-firing optical fibers, as well as the methods of using the side-firing system and the side-firing optical fibers may be used in the treatment of other conditions. Additional objects and advantages of the disclosure will be set forth in part in the description which follows, and in part will be obvious from the description, or may be learned by practice of the disclosure. The objects and advantages of the disclosure may be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the disclosure and together with the description, serve to explain the principles of the invention.

DESCRIPTION OF THE EMBODIMENTS

Reference will now be made in detail to the present embodiments (exemplary embodiments) of the disclosure, examples of which are illustrated in the accompanying drawings. Wherever possible, the same reference numbers will be used throughout the drawings to refer to the same or like parts.

The devices and methods described herein are generally related to an optical fiber configured to treat an area within a body of a patient. Specifically, the optical fiber can be used to transmit laser energy from a laser source to a target treatment area that is disposed lateral to a distal end portion of the optical fiber. One end of the optical fiber, the proximal end portion, can be coupled to the laser source while the other end of the optical fiber, the distal end portion, can be inserted into the patient's body to provide the laser treatment.

The optical fiber can have a surface non-normal to a longitudinal axis of a distal end portion of the optical fiber. The surface can be referred to as an angled surface and can be at the distal end of the optical fiber. The angled surface can define a portion of an interface (can be referred to as a reflective interface) configured to redirect laser energy propagated from within the optical fiber and incident on the interface to a direction offset (e.g., a lateral direction, a side-firing direction) from the longitudinal axis toward the target treatment area. The laser energy redirected via the interface can be referred to as lateral laser energy, redirected laser energy, or side-fired laser energy. Because the optical fiber is configured to redirect laser energy in, for example, a lateral direction, the optical fiber can be referred to as a side-firing optical fiber. In some embodiments, the distal end portion of the optical fiber can be referred to as a side-firing portion or a laterally-firing portion. The optical fiber and/or laser source can be included in an optical fiber system (also can be referred to as a side-fire system).

The angled surface of the optical fiber can be disposed within a doped silica component (e.g., a doped silica cap) that is fused to the optical fiber. Redirected laser energy can be transmitted through a portion of the doped silica component. The doped silica component and the angled surface of the optical component can define an enclosure. An index of refraction of the doped silica component can be defined to promote total or substantially total internal reflection of, for example, leaked/stray laser energy from within the optical fiber and incident on an interface defined by the doped silica component and optical fiber. By internally reflecting the leaked/stray laser energy, the leaked/stray energy can be substantially prevented from, for example, adversely affecting the mechanical and/or optical properties of the side-tiring optical fiber. In some embodiments, the index of refraction can be defined at least in part by a doping concentration of a dopant (e.g., a fluorine dopant, a chlorine dopant, a rare-earth dopant, a germanium dopant, an alkali metal dopant, an alkali metal oxide dopant, etc.) within the silica component. The optical fiber can be optionally doped with any dopant that can be used to dope the silica component (to make a doped silica component), and vice versa.

In some embodiments, the doped silica component can be at least partially formed after being fused to an optical fiber that has an angled surface. In some embodiments, a doped silica cap can be formed from, for example, a doped silica pre-form before being fused to an optical fiber that has, for example, an angled surface. In some embodiments, an outer cover, such as a metallic cap or ceramic cap, can be coupled to the doped silica component. The outer cover can be substantially opaque to a spectral region of electromagnetic radiation associated with the laser energy propagated within the optical fiber. The outer cover can have a transmissive portion (e.g., a window) through which redirected laser energy can be transmitted.

The devices and methods described herein can be used in treating symptoms related to, for example, an enlarged prostate gland, a condition known as Benign Prostatic Hyperplasia (BPH). BPH is a common condition in which the prostate becomes enlarged with aging. The prostate is a gland that is part of the male reproductive system. The prostate gland includes two lobes that are enclosed by an outer layer of tissue and is located below the bladder and surrounding the urethra, the canal through which urine passes out of the body. Prostate growth can occur in different types of tissue and can affect men differently. As a result of these differences, treatment varies in each case. No cure for BPH exists, and once the prostate begins to enlarge, it often continues, unless medical treatment is initiated.

Patients who develop symptoms associated with BPH generally require some form of treatment. When the prostate gland is mildly enlarged, research studies indicate that early treatment may not be needed because the symptoms can clear up without treatment in as many as one-third of cases. Instead of immediate treatment, regular checkups are recommended. Only if the condition presents a health risk, or the symptoms result in major discomfort or inconvenience to the patient, is treatment generally recommended. Current forms of treatment include drug treatment, minimally-invasive therapy, and surgical treatment. Drug treatment is not effective in all cases and a number of medical procedures have been developed to relieve BPH symptoms that are less invasive than conventional surgery.

While drug treatments and minimally-invasive procedures have proven helpful for some patients, many doctors still recommend surgical removal of the enlarged part of the prostate as the most appropriate long-term solution for patients with BPH. For the majority of cases that require surgery, a procedure known as Transurethral Resection of the Prostate (TURP) is used to relieve BPH symptoms. In this procedure, the medical practitioner inserts an instrument called a resectoscope into and through the urethra to remove the obstructing tissue. The resectoscope also provides irrigating fluids that carry away the removed tissue to the bladder.

More recently, laser-based surgical procedures employing side-firing optical fibers and high-power laser sources have been used to remove obstructing prostate tissue. In these procedures, a doctor passes the optical fiber through the urethra using a cystoscope, a specialized endoscope with a small camera on the end, and then delivers multiple bursts of laser energy to destroy some of the enlarged prostate tissue and to shrink the size of the prostate. Patients who undergo laser surgery usually do not require overnight hospitalization, and in most cases, the catheter is removed the same day or the morning following the procedure. Generally, less bleeding occurs with laser surgery and recovery times tend to be shorter than those of traditional procedures such as TURP surgery.

A common laser-based surgical procedure is Holmium Laser Enucleation of the Prostate (HoLEP). In this procedure, a holmium:YAG (Ho:YAG) laser is used to remove obstructive prostate tissue. The Ho:YAG surgical laser is a solid-state, pulsed laser that emits light at a wavelength of approximately 2100 nanometers (nm). This wavelength of light is particularly useful for tissue ablation as it is strongly absorbed by water. An advantage of Ho:YAG lasers is that they can be used for both tissue cutting and for coagulation. Another common laser surgery procedure is Holmium Laser Ablation of the Prostate (HoLAP), where a Ho:YAG laser is used to vaporize obstructive prostate tissue. The decision whether to use HoLAP or HoLEP is based primarily on the size of the prostate. For example, ablation may be preferred when the prostate is smaller than 60 cubic centimeters (cc). Laser-based surgical procedures, such as HoLAP and HoLEP, are often preferred because they produce similar results to those obtained from TURP surgery while having fewer complications and requiring shorter hospital stay, shorter catheterization time, and shorter recovery time.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., a medical practitioner, a medical practitioner, a nurse, a technician, etc.) who would insert the medical device into the patient. Thus, for example, the optical fiber end inserted inside a patient's body would be the distal end of the optical fiber, while the optical fiber end outside a patient's body would be the proximal end of the optical fiber.

Figure 1:
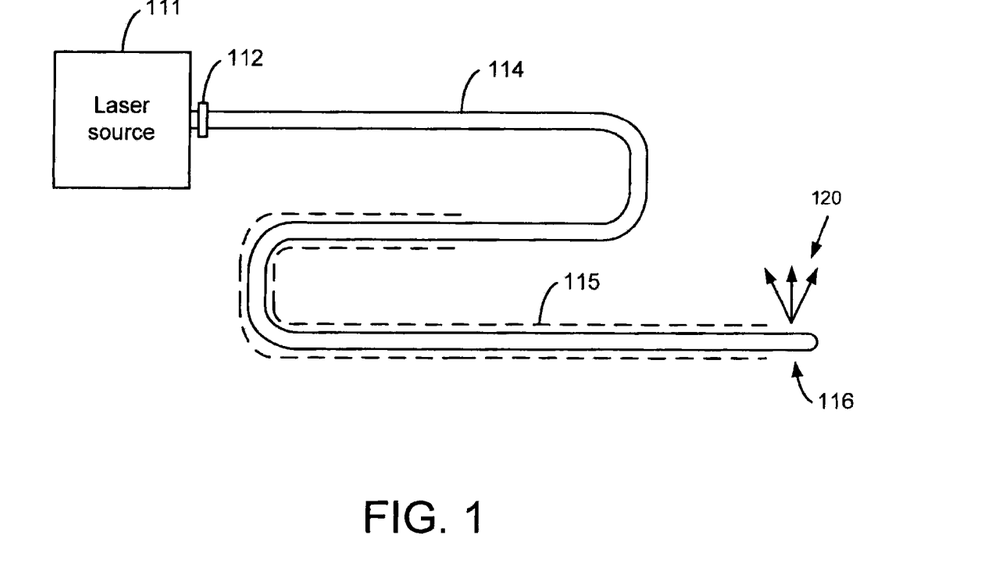
FIG. 1 is a schematic diagram of a side-tire system, according to an embodiment.

FIG. 1 is a schematic diagram of a side-fire system 110, according to an embodiment. The side-fire system 110 can include a laser source 111, an optical coupler 112, a side-fire member 114, and a distal end portion 116. The side-firing system 110 also includes a suitable catheter or endoscope 115 for inserting the distal end portion 116 into a patient's body.

The laser source 111 can be configured to generate laser energy that can be propagated within the side-fire member 114, for example, during a surgical procedure. The laser source 111 can include, for example, a Ho:YAG laser source, a neodymium-doped: YAG (Nd:YAG) laser source, a semiconductor laser diode, and/or a laser source employing a non-linear element (e.g., a laser source that includes a potassium-titanyl phosphate crystal (KTP) laser source). In some embodiments, more than one laser source can be used during a surgical procedure.

In some embodiments, the laser source 111 can also have a control module (not shown) configured to control (e.g., to set, to modify) a timing, a wavelength, and/or a power of laser energy emitted from the laser source 111. In some embodiments, the control module can also be configured to perform various functions such as laser selection, filtering, temperature compensation, and/or Q-switching. The control module can be a hardware-based control module and/or a software-based control module that can include, for example, a processor and/or a memory.

The side-fire member 114 can be coupled to the laser source 111 through the optical coupler 112. The optical coupler 112 can be, for example, a Sub-Miniature A (SMA) connector. The proximal end of the side-fire member 114 can be configured to receive laser energy from the laser source 111, and the distal end of the side-fire member 114 can be configured to output the laser energy 120 through the distal end portion 116. The side-fire member 114 can include an optical fiber that has, for example, a fiber core, one or more cladding layers disposed around the fiber core, a buffer layer disposed around the cladding layer(s), and a jacket (disposed around the buffer layer). In some embodiments, the buffer layer can be referred to as a cladding layer.

In some embodiments, the fiber core can be made of a suitable material for the transmission of laser energy from the laser source 111. In some embodiments, for example, the fiber core can be made of silica with a low hydroxyl ($OH^-$) ion residual concentration. Laser energy wavelengths ranging from about 500 nm to about 2100 nm can be propagated within the fiber core during a surgical procedure. An example of low hydroxyl (low-OH) fibers used in medical devices is described in U.S. Pat. No. 7,169,140 to Kume, the disclosure of which is incorporated herein by reference in its entirety. The fiber core can be a multi-mode fiber core and can have a step or graded index profile. The fiber core can also be doped with a dopant (e.g., an amplifying dopant). The cladding can be a single or a double cladding that can be made of a hard polymer or silica. The buffer (which can function as a cladding layer) can be made of a hard polymer or acrylate, for example. When the optical fiber includes a jacket, the jacket can be made of Tefzel®, for example, or can be made of other polymer-based substances.

The distal end portion 116 can include one or more surfaces that can individually or collectively operate to redirect laser energy in a direction non-parallel (e.g., a lateral direction) to a longitudinal axis or a centerline of the distal end of the fiber core. Such a surface can be an angled surface defined by, for example, the fiber core and/or one or more cladding layers about the fiber core. The angled surface can be non-normal to a longitudinal axis of a distal end portion of the optical fiber. In some embodiments, the surface can be, for example, a reflecting member with a multilayer dielectric coating on an angled surface. More details related to a reflecting member are set forth in co-pending patent application Ser. No. 61/054,280, entitled, "Side-Firing Laser Fiber with Protective Tip and Related Methods," filed May 19, 2008, which is incorporated herein by reference in its entirety.

The surface(s) configured to redirect laser energy can be disposed within a doped silica component at the distal end portion 116 of the side-fire member 114. The doped silica component can be fused (e.g., heat-fused) to a portion of the side-fire member 114. For example, the doped silica component can be heat-fused to a cladding layer of the side-fire member 114. The doped silica component can define at least a portion of an enclosure. When the doped silica component defines at least a portion of an enclosure, the doped silica component can be referred to as a doped silica cap. In some embodiments, an outer cover, such as a metallic cap, can be coupled to an outer surface of the doped silica component.

In some embodiments, the endoscope 115 can define one or more lumens (sometimes referred to as working channels). In some embodiments, the endoscope 115 can include a single lumen that can receive therethrough various components such as the side-fire member 114. The endoscope 115 can have a proximal end configured to receive the distal end portion 116 of the side-fire member 114 and a distal end configured to be inserted into a patient's body for positioning the distal end portion 116 of the side-fire member 114 in an appropriate location for a laser-based surgical procedure. For example, to relieve symptoms associated with BPH, the endoscope 115 can be used to place the optical-fiber distal end portion 116 at or near the enlarged portion of the prostate gland. The endoscope 115 can include an elongate portion that can be sufficiently flexible (or rigid) to allow the elongate portion to be maneuvered within the body.

The endoscope 115 can also be configured to receive various medical devices or tools through one or more lumens of the endoscope, such as, for example, irrigation and/or suction devices, forceps, drills, snares, needles, etc. An example of such an endoscope with multiple lumens is described in U.S. Pat. No. 6,296,608 to Daniels et al., the disclosure of which is incorporated herein by reference in its entirety. In some embodiments, a fluid channel (not shown) is defined by the endoscope 115 and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscope 115, for example, and coupled to a proximal end portion of an optical fiber that can be disposed within a lumen of the endoscope 115. Such an embodiment allows a medical practitioner to view the interior of a patient's body through the eyepiece.

Figure 2:
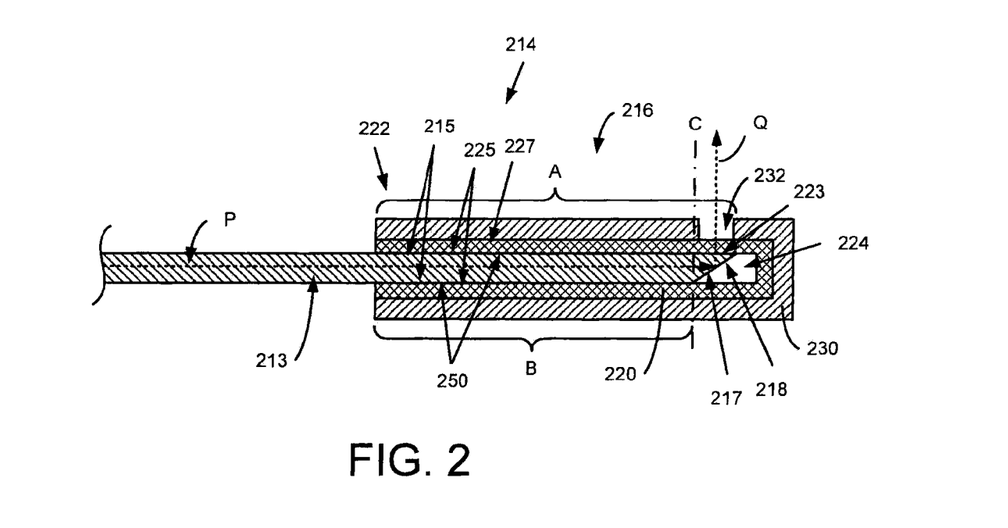
FIG. 2 is a side cross-sectional view of a distal end portion of a side-fire member that has a doped silica component, according to an embodiment.

FIG. 2 is a side cross-sectional view of a distal end portion 216 of a side-fire member 214 that has a doped silica component 220, according to an embodiment. An outer cover 230 (e.g., a metallic cover, a plastic cover) may optionally be coupled to and disposed outside of the doped silica component 220. As shown in FIG. 2, laser energy P that is propagated along a longitudinal axis (or centerline) of an optical fiber 213 of the side-fire member 214 is redirected by an interface 218 defined by an angled surface 217 and a gas (or a liquid) 224 within a cavity defined by the doped silica component 220. In some embodiments, the gas can be air. The redirected laser energy Q is transmitted through a portion of the doped silica component 220 and an opening 232 defined by the outer cover 230. In other words, the laser energy P is transmitted within an optical path along the longitudinal axis (or centerline) of the optical fiber 213, and the redirected laser energy Q is transmitted within an optical path that intersects the doped silica component 220 and the opening 232. In some embodiments, the optical path(s) can include multiple segments. Although not shown, the optical fiber 213 can have, for example, a fiber core, one or more cladding layers about the fiber core, and/or a buffer layer (which can function as a cladding layer or the only cladding layer).

An inner surface 225 of the doped silica component 220 is heat-fused to an outer surface 215 of the optical fiber 213. Specifically, the inner surface 215 is heat-fused over an entire area of the outer surface 215 of the optical fiber 213 that is disposed within the doped silica component 220 (except for the angled surface 217, which is not part of the outer surface 215). In other words, any portion of the outer surface 215 of the optical fiber 213 that is substantially parallel to, and disposed within the doped silica component 220, is fused to the inner surface 225 of the doped silica component 220. Because the optical fiber 213 has an angled surface 217, a heat-fused length A along a top side of the optical fiber 213 is longer than a heat-fused length B along a bottom side of the optical fiber 213.

In some embodiments, less than the entire area of the outer surface 215 of the optical fiber 213 can be heat-fused to the inner surface 225 of the doped silica component 220. In some embodiments, a portion of the outer surface 215 of the optical fiber 213 that is proximal to a plane C, which is at a proximal end of the angled surface 217 and substantially normal to a longitudinal axis of the optical fiber 213, can be heat-fused to the doped silica component 220. In some embodiments, multiple locations along the outer surface 215 of the optical fiber 213 can be heat-fused to the inner surface 225 of the doped silica component 220. For example, a portion of the outer surface 215 near the proximal end 222 of the doped silica component 220 and/or a portion of the outer surface 215 near the angled surface 217 can be heat fused to the inner surface of the doped silica component 220. In some embodiments, two or more circumferential portions of the outer surface 215 can be heat-fused to the doped silica component 220. In some embodiments, the heat-fused portions do not continuously surround the optical fiber 213. In other words, just a top portion (e.g., a first portion) and/or a bottom portion (e.g., a portion opposite the first portion) of the outer surface 215 of the optical fiber 213 can be heat-fused to the doped silica component 220. In some embodiments, a portion 223 of the doped silica component 220 and inner surface 225 through which the laser will be directed may be heat-fused (to prevent unwanted reflection from an unfused interface between the doped silica component 220 and inner surface 225). The heat-fused area can be sufficiently large to provide mechanical stability (e.g., resistance to shear forces) between the optical fiber 213 and the doped silica component 220. As shown in FIG. 2, an interface 250 is defined by the inner surface 225 of the doped silica component 220 and an outer surface 215 of the optical fiber 213.

The doped silica component 220 has an index of refraction less than an index of refraction of the outer surface 215 of the optical fiber 213. In some embodiments, the doped silica component 220 can be doped with, for example, a concentration of fluorine. Because of the difference in the indices of refraction, a portion of the laser energy P propagated within the optical fiber 213 and incident on the interface 250 can be totally or substantially totally internally reflected within the optical fiber 213. If the optical fiber 213 has a cladding layer (not shown), a portion of the laser energy P propagated within the cladding layer and incident on the interface 250 can be totally or substantially totally internally reflected within the cladding layer.

The angle of incidence of the redirected laser energy Q on the interface 250 can be defined so that the redirected laser energy Q is transmitted through the interface 250 rather than reflected. As shown in FIG. 2, a path of the redirected laser energy Q can be substantially normal and/or non-normal to the surfaces (e.g., the outer surface 215, the inner surface 225) that defined the interface 250. More details related to internal reflection and angles of incidence are described in connection with FIG. 3.

The index of refraction of the doped silica component 220 can be defined by the concentration of a dopant (e.g., fluorine) within the doped silica component 220. In some embodiments, the doping concentration of the doped silica component 220 can be substantially uniform. In some embodiments, the doping concentration at the inner surface 225 of the doped silica component 220 can be lower than, for example, an outer surface 227 of the doped silica component 220, and vice versa. Likewise, the index of refraction of the outer surface 215 of the optical fiber 213 can be defined by a concentration of a dopant. In some embodiments, the doping concentration of the outer surface 215 of the optical fiber 213 can be substantially uniform. In some embodiments, the index of refraction, as defined by a dopant concentration, at the outer surface 215 of the optical fiber 213 can be lower than, or higher than, for example, at an inner portion of the optical fiber 213, and vice versa.

The outer cover 230 is configured to keep stray laser energy (e.g., a portion of stray laser energy from laser energy P) from being transmitted in an undesirable direction out of the side-fire member 214. The outer cover 230 can be, for example, adhesively coupled to, mechanically coupled to (e.g., mechanically coupled via a screw) and/or press fit around the doped silica component 220. Accordingly, the outer cover 230 can be substantially opaque to the laser energy P and/or configured to reflect and/or absorb stray laser energy within (e.g., internal to) the distal end portion 216 of the side-fire member 214. The outer cover 230 can be made of a metallic material such as a surgical (e.g., medical) grade stainless steel, a plastic, or other material with like properties. In some instances, the outer cover 230 can be made of a ceramic material (e.g., alumina) because certain ceramics have stable material characteristics at high-temperatures and/or have a high reflectance value at desirable operating wavelengths of the laser energy P. The outer cover 230 can also provide protection (e.g., mechanical protection) to the distal end portion 216 of the side-fire member 214.

In some embodiments, rather than an opening 232, the outer cover 230 can include a transmissive material (not shown) through which the redirected laser energy Q can be transmitted for surgical treatment. The transmissive material can be, for example, substantially transparent to a specified spectrum of electromagnetic radiation associated with the redirected laser energy Q. The transmissive material can define, for example, a lens. In some embodiments, the transmissive material can be treated thermally, optically, mechanically, and/or chemically to define a desirable structural and/or optical characteristic. For example, the optically-transmissive material can be thermally treated during manufacturing using emissions from, for example, a carbon dioxide ($CO_2$) laser source. The transmissive material can be defined such that the redirected laser energy Q can be delivered to a target area in a desirable fashion (e.g., delivered in a focused beam).

Figure 3:
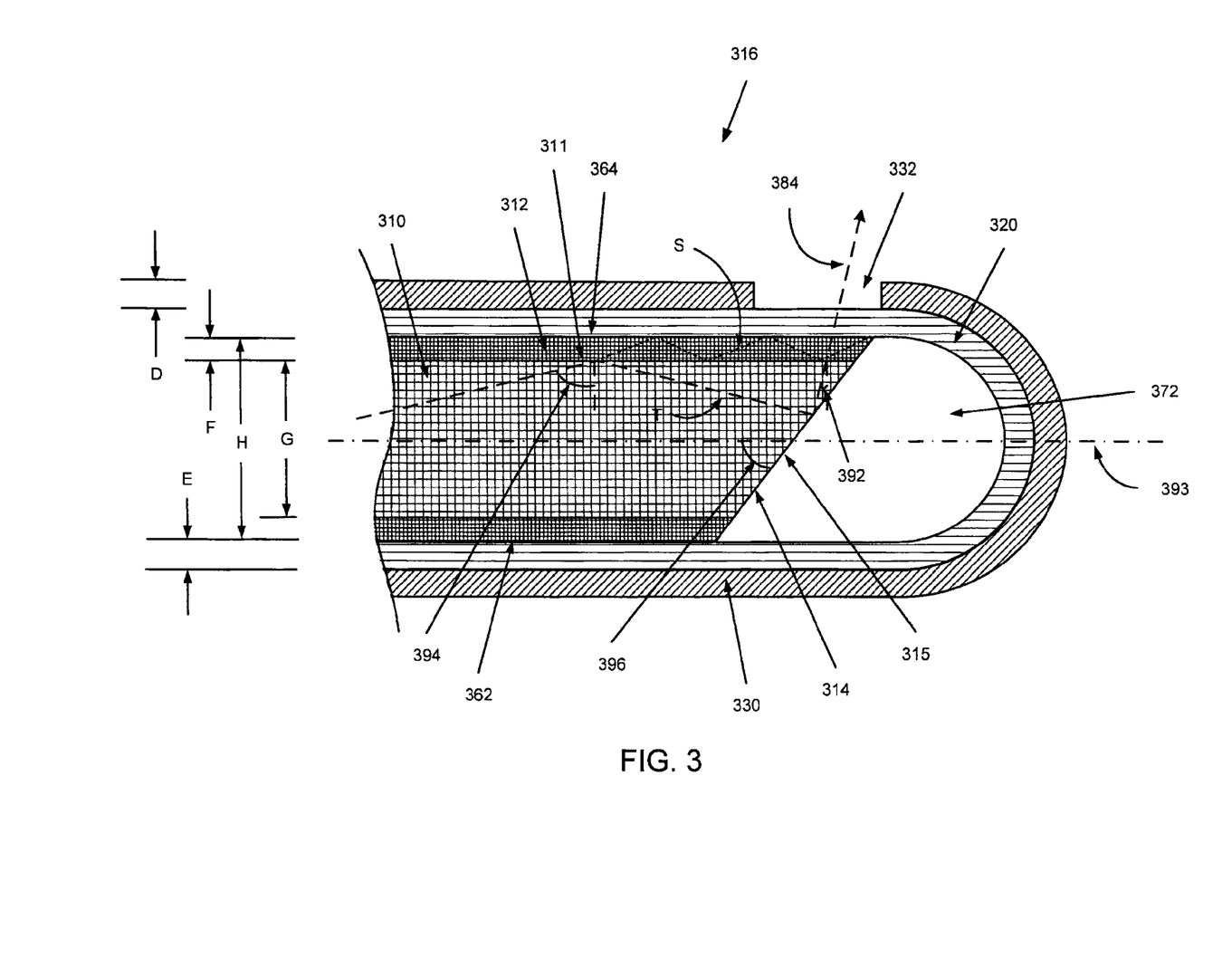
FIG. 3 is a schematic diagram that illustrates a side cross-sectional view of a distal end of a side-fire member, according to an embodiment.

FIG. 3 is a schematic diagram that illustrates a side cross-sectional view of a distal end 316 of a side-fire member, according to an embodiment. As shown in FIG. 3, an outer cover 330 is disposed outside of a doped silica component 320. The doped silica component 320 is heat-fused to a cladding layer 312 that is disposed outside of a fiber core 310 of an optical fiber within the side-fire member. The optical fiber has an angled surface 314 that is non-normal to a longitudinal axis 393 of the distal end 316. As shown in FIG. 3, the angled surface 314 and an air-filled cavity 372 define an interface 315 configured to redirect laser energy T that is propagated from within the optical fiber and is incident on the interface 315. The redirected laser energy 384 is transmitted through the doped silica component 320 and out of an opening 332 within the outer cover 330. The cavity 372 can be defined by the doped silica component 320 and the angled surface 314.

The doped silica component 320 has an index of refraction that is less than an index of refraction of the cladding layer 312. The index of refraction of the cladding layer 312 is less than an index of refraction of the fiber core 310 of the optical fiber. Accordingly, the laser energy T that is incident on an interface 311 defined by the cladding layer 312 and the fiber core 310 is internally reflected within the fiber core 310 as shown in FIG. 3. Portions of laser energy S that leak into the cladding layer 312 are internally reflected by an interface 364 defined by the doped silica component 320 and the cladding layer 312.

As shown in FIG. 3, at least a portion of the redirected laser energy 384 is substantially or totally transmitted through at least a portion of the cladding layer 312 and at least a portion of the doped silica component 320. In other words, an optical path of the redirected laser energy 384 intersects at least a portion of the cladding layer 312 and at least a portion of the doped silica component 320. An angle of incidence 392 (relative to a reference line normal to the interface 311 and interface 364) of the redirected laser energy 384 is sufficiently small that the redirected laser energy 384 is substantially or totally transmitted through the doped silica component 320.

As shown in FIG. 3, a portion of the laser energy S (from laser energy T) is leaked into the cladding layer 312. The laser energy S can also be referred to as stray/leaked laser energy. The indices of refraction of refraction the cladding layer 312 and the doped silica component 320, respectively, are defined so that the laser energy S is internally reflected within the cladding layer 312 rather than transmitted through the doped silica component 320 (and incident on the outer cover 330). This can prevent or reduce undesirable amounts of laser energy S from being transmitted through the doped silica component 320 and incident on the outer cover 330, which in turn can prevent or reduce the distal end 316 of the side-fire member from being damaged. For example, this can prevent or reduce the outer cover 330 from being overheated and can becoming decoupled from the doped silica component 320.

In some embodiments, the indices of refraction of the cladding layer 312 and the doped silica component 320, respectively, can be defined so that a desirable range of angles of incidence of the redirected laser energy 384 will be transmitted through the doped silica component 320 while unacceptable levels of laser energy S within the cladding layer 312 will not be transmitted through the doped silica component 320. Because the interface 364 is a total-internal-reflection interface, a relatively large inner surface area of the doped silica component 320 can be heat-fused to the cladding layer 312 with a substantially reduced possibility that the stray laser energy S will be undesirably transmitted into the doped silica component 320 through the heat-fused area. A relatively large heat-fused area promotes a strong bond between the doped silica component 320 and the cladding layer 312 that can be substantially resistant to tensile forces (e.g., forces in the distal or proximal direction along the longitudinal axis 393). If the index of refraction of the doped silica component were substantially equal to that of the cladding layer, an undesirable (e.g., a damaging) percentage of the stray laser energy could be transmitted into the doped silica component and incident on the outer cover; the amount of laser energy transmitted into the doped silica component would be substantially increased with a larger heat-fused area.

As shown in FIG. 3, an angle of incidence 394 of the laser energy T propagated within the fiber core 310 (relative to a line normal to interface 311 and interface 364) is sufficiently large that the laser energy T is substantially or totally internally reflected within the fiber core. In some embodiments, the indices of refraction the fiber core 310 and the cladding layer 312, respectively, can be defined so that a specified range of the angles of incidence that will reflect the laser energy T within the fiber core 310 (or range of angles of incidence that will transmit laser energy T through the cladding layer 312) can be achieved.

An angle 396 of the angled surface 314 relative to the longitudinal axis can be defined (e.g., determined, selected, designed) based on at least one of several parameters. For example, the angle 396 can be defined based on the wavelength of the laser energy T (and/or redirected laser energy 384), the numerical aperture of the fiber core 310, the exit or output location for the redirected laser energy 384, anticipated angle of incidence of the laser energy T, and/or the optical properties of the doped silica component 320. Moreover, the optical properties of the air-filled cavity 372 can also be used in determining an appropriate angle 396 for the angled surface 314. For example, an angle 396 of 35 degrees can result in the laser or optical beam being laterally reflected at an angle of about 70 degrees from the longitudinal axis 393 of the distal end 316.

A fiber core 310 of the side-fire member can have an outer diameter G, for example, between approximately 20 micrometers (μm) to 1200 μm. The cladding layer 312 can have a thickness F of between, for example, approximately 5 μm to 120 μm. In some embodiments, the outer diameter H of the cladding layer 312 can be 1 to 1.3 times greater than the outer diameter G of the fiber core 310. The doped silica component 320 can have a thickness E of between, for example, approximately 5 μm to several millimeters. The outer cover 330 can have a thickness D of several micrometers to several millimeters. Although not shown, in some embodiments, the outer cover 330 can include a low-profile cover (e.g., a coating or a sleeve).

Figure 4:
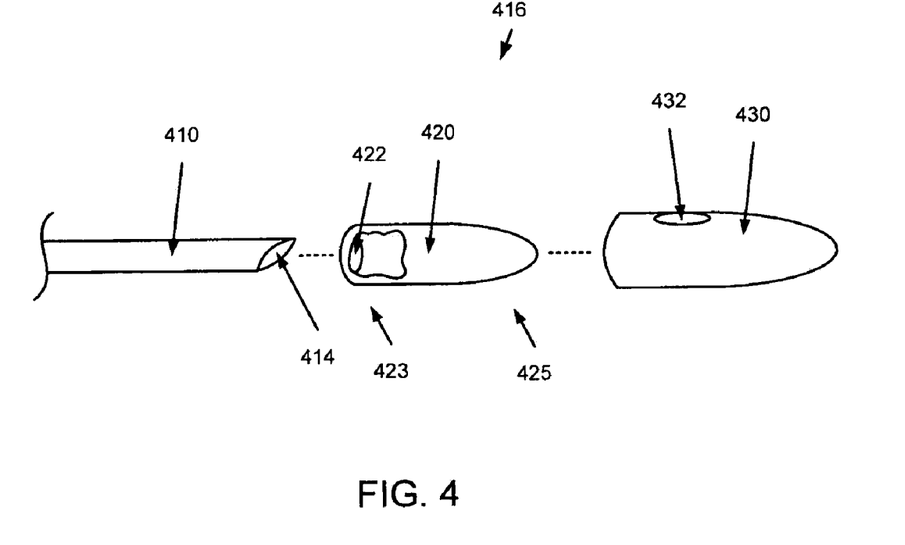
FIG. 4 is a schematic diagram that illustrates an exploded view of a distal end of a side-fire member, according to an embodiment.

FIG. 4 is a schematic diagram that illustrates an exploded view of a distal end 416 of a side-fire member, according to an embodiment. As shown in FIG. 4, the distal end includes an optical fiber 410, a doped silica component 420, and an outer cover 430. The optical fiber 410 has an angled surface 414, and the outer cover 430 has a transmissive portion 432. In some embodiments, the transmissive portion 432 can be an opening.

In some embodiments, the angled surface 414 of the optical fiber 410 can be defined before the doped silica component 420 is moved over the optical fiber 410 and heat-fused to the optical fiber 410. The angled surface 414 can be, for example, mechanically defined by grinding and/or polishing a distal end of a cleaved optical fiber using, for example, a mechanical device (e.g., mechanical grinder) and/or a laser source.

As shown in FIG. 4, the doped silica component 420 has an opening 422 (shown through the cut-away) at a proximal end 423. The doped silica component 420 has a closed distal end 425 opposite the opening 422 at the proximal end 423. In some embodiments, the closed distal end 425 can be defined before the doped silica component 420 is moved over the optical fiber 410 and heat-fused to the optical fiber 410. In some embodiments, the closed distal end 425 can be defined after the doped silica component 420 has been heat-fused to the optical fiber 410. More details related to defining a closed distal end of a doped silica component 420 after being heat-fused to an optical fiber 410 are described in connection with FIGS. 5A-5D.

In some embodiments, the transmissive portion 432 can include a transmissive material (e.g., a lens) that is inserted into an opening within the outer cover 430. In some embodiments, the transmissive material can be inserted into the opening before the outer cover 430 is moved over and coupled to the doped silica component 420. In some embodiments, the outer cover 430 can be, for example, adhesively bonded to the doped silica component 420. In some embodiments, the outer cover 430 can be coupled to the doped silica component 420 before the doped silica component 420 is coupled to the optical fiber 410.

Figure 5A:
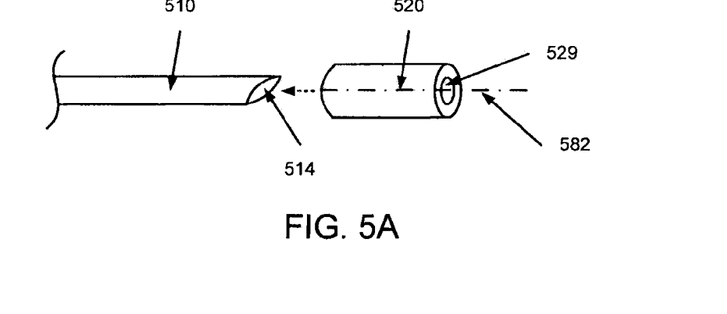
FIG. 5A is a schematic diagram that illustrates a doped silica component and an optical fiber before the doped silica component is disposed over the optical fiber, according to an embodiment.
Figure 5B:
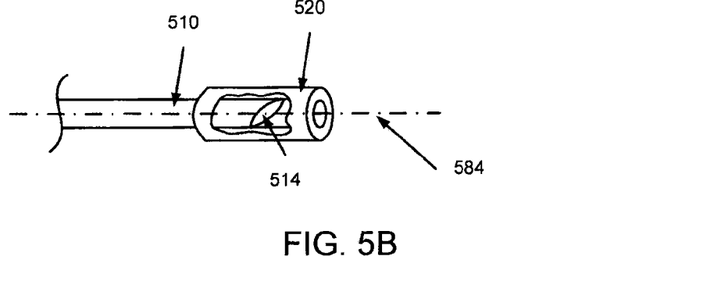
FIG. 5B is a schematic diagram that illustrates a doped silica component after being disposed over an optical fiber, according to an embodiment.

FIGS. 5A-5D are schematic diagrams that collectively illustrate a method for producing a side-fire member, according to an embodiment. FIG. 5A is a schematic diagram that illustrates a doped silica component 520 and an optical fiber 510 before the doped silica component 520 is disposed over the optical fiber 510, according to an embodiment. FIG. 5B is a schematic diagram that illustrates the doped silica component 520 after being disposed (e.g., placed) over the optical fiber 510, according to an embodiment. As shown in FIG. 5A, the optical fiber 510 has an angled surface 514 before the doped silica component 520 is disposed over the optical fiber 510.

The doped silica component 520 has a bore 529 (e.g., a lumen) along a longitudinal axis 582 of the doped silica component 520. The bore 529 of the doped silica component 520 is in fluid communication with an opening at each end (along the longitudinal axis 582) of the doped silica component 520. The doped silica component 520 can be cut from a length of a doped silica tubular (e.g., cylindrical) pre-form (not shown). The doped silica component 520 component can be cut from the pre-form using, for example, a laser energy cutting instrument or a mechanical cutting instrument. The pre-form can be cut along a plane that is substantially normal to a longitudinal axis of the pre-form.

In some embodiments, the doped silica component 520 can be uniformly or non-uniformly doped with, for example, fluorine and/or another suitable dopant. In some embodiments, the doped silica component 520 can be between 50 mm to 10 cm long. In some embodiments, the doped silica tubular pre-form can have a doping concentration that is higher near an inner surface that defines the bore than at an outer surface of the pre-form.

In some embodiments, the size of the bore 529 can be increased before being disposed over the optical fiber 510. In some embodiments, the size of the bore 529 can be increased by removing a portion of a wall defining the bore 529 with, for example, a reaming device. An inner diameter of the bore 529 can be defined so that it is, for example, at least a few micrometers larger than an outer diameter of the optical fiber 510.

After the doped silica component 520 has been disposed over the optical fiber 510, the doped silica component 520 can be heat-fused to the optical fiber 510. In some embodiments, the doped silica component 520 and optical fiber 510 can be heated using, for example, a heating source (e.g., a torch, an electrical heating element, a laser source) until the doped silica component 520 and optical fiber 510 are fused. The doped silica component 520 and optical fiber 510 can be rotated about a longitudinal axis 584 of the optical fiber 510 while being heated.

Figure 5C:
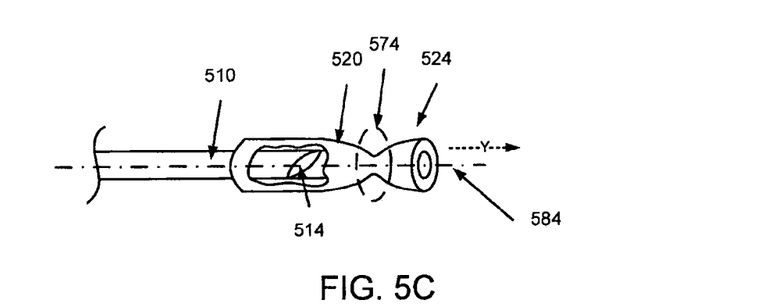
FIG. 5C is a schematic diagram that illustrates a distal end of a doped silica component being heated and pulled, according to an embodiment.

FIG. 5C is a schematic diagram that illustrates a distal end 524 of the doped silica component 520 being heated and pulled, according to an embodiment. The distal end 524 is being heated in a zone 574 while being pulled in direction Y until an enclosure 572 (shown in FIG. 5D) is formed. In other words, a force in direction Y (away from the angled surface 514) is applied on the distal end 524 while it is being heated. The doped silica component 520 can be heated until the doped silica component 520 softens and can be pulled. As the distal end 524 of the doped silica component 520 is heated and pulled, the doped silica component 520 plastically deforms until at least a portion of the distal end 524 is separated from the doped silica component 520 to define the shape of the doped silica component 520 shown in FIG. 5D.

In some embodiments, the heating and/or pulling discussed in connection with FIG. 5C are not performed coincidentally. For example, a portion of the distal end 524 can be heated before the distal end 524 is pulled. In some embodiments, the optical fiber 510 and doped silica component 520 can be rotated, for example, around the longitudinal axis 584 while being heated and/or pulled. In some embodiments, the heating associated with FIG. 5B (during fusing) and the heating associated with FIG. 5C can be performed using the same heating source and/or can be performed within the same heating cycle. In some embodiments, the heating associated with FIG. 5B and the heating associated with FIG. 5C can be performed separately (e.g., different space and time) using different heating sources.

Figure 5D:
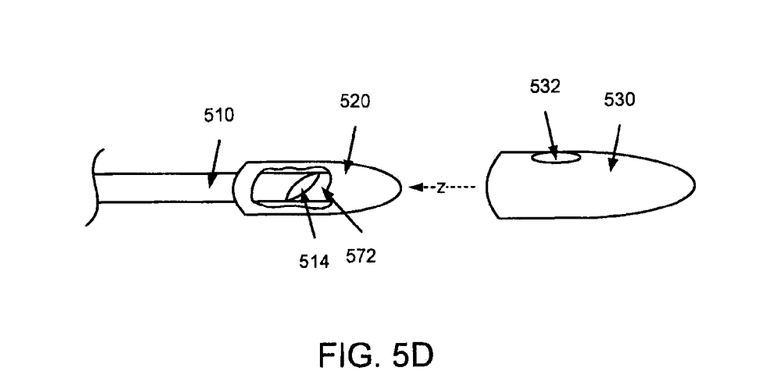
FIG. 5D is a schematic diagram that illustrates an outer cover and a doped silica component heat-fused to an optical fiber, according to an embodiment.

FIG. 5D is a schematic diagram that illustrates an outer cover 530 and a doped silica component 520 heat-fused to an optical fiber 520, according to an embodiment. An enclosure 572 is defined by the angled surface 514 and the doped silica component 520. As shown in 5D, the outer cover 530 can be moved in direction Z and coupled to the doped silica component 520. In some embodiments, at least a portion of a transmissive portion 532 is disposed within (e.g., intersects) an optical path of laser energy redirected by the angled surface 514.

Figure 6:
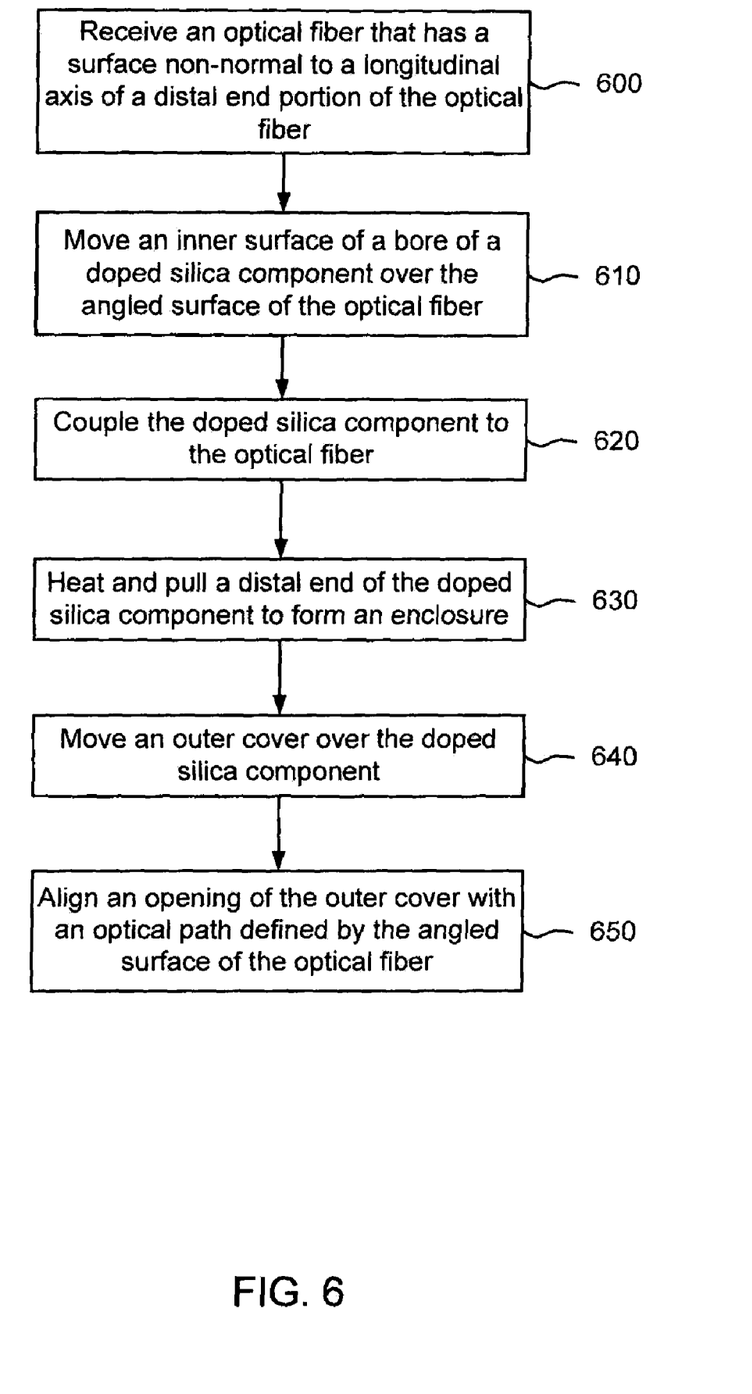
FIG. 6 is a flowchart that illustrates a method for producing a distal end of a side-fire member, according to an embodiment.

FIG. 6 is a flowchart that illustrates a method for producing a distal end of a side-fire member, according to an embodiment. As shown in FIG. 6, an optical fiber that has a surface non-normal to a longitudinal axis of a distal end portion of the optical fiber is received at 600. The non-normal surface can be referred to as an angled surface.

An inner surface of a bore of a doped silica component is moved over the angled surface of the optical fiber at 610 and the doped silica component is coupled to the optical fiber at 620. In some embodiments, a shape and/or size of at least a portion of the bore can be changed before being moved over the angled surface and coupled to the optical fiber.

A distal end of the doped silica component is heated and pulled to define an enclosure at 630. The enclosure can be defined, at least in part by the angled surface of the optical fiber and an inner surface of the doped silica component.

An outer cover is moved over the doped silica component at 640 and an opening of the outer cap is aligned with an optical path defined by the angled surface of the optical fiber at 650. The outer cover can be, for example, adhesively bonded to the doped silica component.

Other embodiments of the disclosure will be apparent to those skilled in the art from consideration of the specification and practice of the disclosure herein. It is intended that the specification and examples be considered as exemplary only, with a true scope and spirit of the invention being indicated by the following claims.

What is claimed is:

1. An apparatus, comprising:
an optical fiber including a surface non-normal to a longitudinal axis of a distal end portion of the optical fiber, wherein the surface defines a portion of an interface configured to redirect electromagnetic radiation propagated from within the optical fiber and incident on the interface to a direction offset from the longitudinal axis;
a doped silica cap, the doped silica cap being fused to the optical fiber such that the surface of the optical fiber is disposed within a cavity defined by the doped silica cap; and
a metallic cap coupled to the doped silica cap, wherein the metallic cap includes an inner surface configured to redirect electromagnetic radiation incident on the inner surface of the metallic cap into the cavity defined by the doped silica cap.

2. The apparatus of claim 1, wherein the doped silica cap has an index of refraction less than an index of refraction associated with a cladding layer of the optical fiber.

3. The apparatus of claim 1, wherein the doped silica cap is fused to a cladding layer of the optical fiber.

4. The apparatus of claim 1, wherein the doped silica cap is fused to an outer-layer portion of the optical fiber, the doped silica cap is a fluorine-doped silica cap, and the doped silica cap includes a concentration of fluorine greater than a concentration of fluorine of the outer-layer portion of the optical fiber.

5. The apparatus of claim 1, wherein the interface is a first interface and the doped silica cap is fused to a cladding layer of the optical fiber, and wherein the doped silica cap and the cladding layer define a second interface such that electromagnetic radiation propagated within the cladding layer and incident on the second interface is substantially internally reflected within the cladding layer.

6. The apparatus of claim 1, wherein the surface is disposed within a distal end portion of the doped silica cap, and wherein a proximal end portion of the doped silica cap is fused to the optical fiber.

7. The apparatus of claim 1, wherein the surface is included in the distal end portion of the optical fiber, and wherein the doped silica cap is fused to a portion of the optical fiber proximal to the distal end portion of the optical fiber without being fused to the distal end portion of the optical fiber.

8. The apparatus of claim 1,
wherein the metallic cap includes an opening aligned with the direction such that the electromagnetic radiation is transmitted through the opening.

9. A method, comprising:
receiving an optical fiber, the optical fiber including a surface non-normal to a longitudinal axis of a distal end portion of the optical fiber;
moving a doped silica component over the surface of the optical fiber such that the surface of the optical fiber is disposed within a bore;
heating the doped silica component and the optical fiber such that at least a portion of an inner surface of the doped silica component defined by the bore may be fused to at least a portion of an outer surface of the optical fiber; and
moving an outer cap over the doped silica component, wherein the outer cap is substantially opaque to laser energy transmitted from the optical fiber.

10. The method of claim 9, wherein moving the doped silica component includes moving until the surface of the optical fiber is disposed within the bore of the doped silica component.

11. The method of claim 9, wherein the portion of the inner surface of the doped silica component defined by the bore is included in a proximal end of the doped silica component, and wherein the bore of the doped silica component is a bore therethrough.

12. The method of claim 9, wherein the portion of the inner surface of the doped silica component defined by the bore is included in a proximal end of the doped silica component, the bore of the doped silica component being a bore therethrough, the method further comprising:
heating a distal end of the doped silica component such that an enclosure is defined by the distal end of the doped silica component and the optical fiber.

13. The method of claim 9, wherein the heating defines an interface, and wherein the doped silica component includes a doping concentration such that electromagnetic radiation from the optical fiber and incident on the interface is substantially internally reflected within the optical fiber.

14. The method of claim 9, wherein the surface of the optical fiber defines a portion of an interface configured to redirect electromagnetic radiation propagated from within the silica-based optical fiber and incident on the interface to a lateral direction offset from the longitudinal axis; the method further comprising:
moving the outer cap over the doped silica component such that an opening defined by the outer cap is aligned with the lateral direction.

15. An apparatus, comprising:
a doped silica cap;
a distal end portion of an optical fiber that includes a surface disposed within the doped silica cap,
wherein the surface defines at least a portion of an interface configured to redirect laser energy from a first portion of an optical path to a second portion of the optical path non-parallel to the first portion of the optical path, and wherein the second portion of the optical path intersects an outer surface of the doped silica cap; and
an outer cap disposed over at least a portion of the doped silica cap, wherein the outer cap is substantially opaque to laser energy.

16. The apparatus of claim 15, wherein at least a portion of an inner surface of the doped silica cap and at least a portion of an outer surface of the distal end portion of the optical fiber define an interface, and wherein the doped silica cap includes a doping concentration such that electromagnetic radiation from the optical fiber and incident on the interface is substantially internally reflected within the optical fiber.

17. An apparatus, comprising:
an optical fiber including a surface non-normal to a longitudinal axis of a distal end portion of the optical fiber, wherein the surface defines a portion of an interface configured to redirect electromagnetic radiation propagated from within the optical fiber and incident on the interface to a direction offset from the longitudinal axis;
a doped silica cap, the doped silica cap being fused to the optical fiber such that the surface of the optical fiber is disposed within a cavity defined by the doped silica cap; and
a metallic cap coupled to the doped silica cap, wherein the metallic cap includes an opening aligned with the direction such that the electromagnetic radiation is transmitted through the opening.

18. A method, comprising:
- receiving an optical fiber, the optical fiber including a surface non-normal to a longitudinal axis of a distal end portion of the optical fiber, wherein the surface of the optical fiber defines a portion of an interface configured to redirect electromagnetic radiation propagated from within the silica-based optical fiber and incident on the interface to a lateral direction offset from the longitudinal axis;
- moving a doped silica component over the surface of the optical fiber such that the surface of the optical fiber is disposed within a bore;
- heating the doped silica component and the optical fiber such that at least a portion of an inner surface of the doped silica component defined by the bore may be fused to at least a portion of an outer surface of the optical fiber; and
- moving an outer cap over the doped silica component such that an opening defined by the outer cap is aligned with the lateral direction.

19. An apparatus, comprising:
- a doped silica cap;
- a distal end portion of an optical fiber that includes a surface disposed within the doped silica cap, wherein the surface defines at least a portion of an interface configured to redirect laser energy from a first portion of an optical path to a second portion of the optical path non-parallel to the first portion of the optical path, and wherein the second portion of the optical path intersects an outer surface of the doped silica cap; and
- a metallic cap disposed over at least a portion of the doped silica cap, wherein the second portion of the optical path may intersect an opening of the metallic cap.

20. The apparatus of claim 19, wherein at least a portion of an inner surface of the doped silica cap and at least a portion of an outer surface of the distal end portion of the optical fiber define an interface, and wherein the doped silica cap includes a doping concentration such that electromagnetic radiation from the optical fiber and incident on the interface is substantially internally reflected within the optical fiber.

* * * * *